United States Patent
Wakasugi et al.

(10) Patent No.: US 12,320,793 B2
(45) Date of Patent: *Jun. 3, 2025

(54) ANALYSIS METHOD OF 3-METHYL-1-PHENYL-2-PYRAZOLIN-5-ONE ACTIVE PHARMACEUTICAL INGREDIENT, TREATMENT FOR AMYOTROPHIC LATERAL SCLEROSIS, INHIBITION OF PROGRESSION OF AMYOTROPHIC LATERAL SCLEROSIS, AND METHOD OF PRODUCING MEDICAMENT CONTAINING 3-METHYL-1-PHENYL-2-PYRAZOLIN-5-ONE ACTIVE PHARMACEUTICAL INGREDIENT

(71) Applicant: MITSUBISHI TANABE PHARMA CORPORATION, Osaka (JP)

(72) Inventors: Takeshi Wakasugi, Osaka (JP); Aya Sano, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/360,292

(22) Filed: Jul. 27, 2023

(65) Prior Publication Data

US 2023/0366867 A1    Nov. 16, 2023

Related U.S. Application Data

(60) Continuation of application No. 17/730,853, filed on Apr. 27, 2022, now Pat. No. 11,740,219, which is a division of application No. 17/536,947, filed on Nov. 29, 2021, now abandoned, which is a continuation of application No. 16/976,287, filed as application No. PCT/JP2019/007415 on Feb. 27, 2019, now abandoned.

(30) Foreign Application Priority Data

Feb. 28, 2018   (WO) .................. PCT/JP2018/007544

(51) Int. Cl.
| | |
|---|---|
| G01N 33/15 | (2006.01) |
| A61K 31/415 | (2006.01) |
| A61K 31/4152 | (2006.01) |
| C07D 231/26 | (2006.01) |
| G01N 30/02 | (2006.01) |
| G01N 30/04 | (2006.01) |
| G01N 30/06 | (2006.01) |

(52) U.S. Cl.
CPC ........... *G01N 33/15* (2013.01); *A61K 31/415* (2013.01); *A61K 31/4152* (2013.01); *C07D 231/26* (2013.01); *G01N 30/06* (2013.01); *G01N 2030/027* (2013.01); *G01N 2030/042* (2013.01); *G01N 2030/067* (2013.01)

(58) Field of Classification Search
CPC ...... G01N 33/15; G01N 30/06; A61K 31/415; A61K 31/4152
See application file for complete search history.

(56) References Cited

U.S. PATENT DOCUMENTS

| | | | |
|---|---|---|---|
| 4,857,542 A | 8/1989 | Nishi et al. | |
| 7,211,596 B2 | 5/2007 | Yoshida et al. | |
| 9,956,203 B2 | 5/2018 | Ozaki et al. | |
| 10,987,341 B2 | 4/2021 | Hayama et al. | |
| 11,241,416 B2 | 2/2022 | Hayama et al. | |
| 11,740,219 B2 * | 8/2023 | Wakasugi ............ | A61K 31/415 73/61.55 |

FOREIGN PATENT DOCUMENTS

| | | |
|---|---|---|
| CN | 102841170 A | 12/2012 |
| CN | 103454370 A | 12/2013 |
| CN | 106117144 A | 11/2016 |
| JP | S63-132833 A | 6/1988 |
| JP | 05-031523 B2 | 5/1993 |
| JP | 2008-001606 A | 1/2008 |
| JP | 2008-001607 A | 1/2008 |
| JP | 2010-077104 A | 4/2010 |
| WO | WO 02/034264 A1 | 5/2002 |
| WO | WO 2019/031495 A1 | 2/2019 |

OTHER PUBLICATIONS

Li Shuai et al., "Optimization of HPLC determination of phenylhydrazine residues in edaravone" Central South Pharmacy, Aug. 2014, vol. 12 No. 8, pp. 814-816, with English translation.
International Search Report issued May 14, 2019 in PCT/JP2019/007415, filed Feb. 27, 2019, 2 pages.
International Preliminary Report on Patentability issued Sep. 1, 2020 in PCT/JP2019/007415, filed Feb. 27, 2019, 7 pages.

(Continued)

*Primary Examiner* — James D. Anderson
(74) *Attorney, Agent, or Firm* — Oblon, McClelland, Maier & Neustadt, L.L.P.

(57) ABSTRACT

A method of analyzing phenylhydrazine content in a 3-methyl-1-phenyl-2-pyrazolin-5-one active pharmaceutical ingredient includes obtaining a first measured value by measuring a phenylhydrazine content of a standard solution including phenylhydrazine or a salt thereof, a first acidic water and a first water-soluble organic solvent and having a phenylhydrazine concentration of 0.01 µg/mL to 10 µg/mL, obtaining a second measured value by measuring a phenylhydrazine content in a sample solution including a 3-methyl-1-phenyl-2-pyrazolin-5-one active pharmaceutical ingredient, a second acidic water and a second water-soluble organic solvent, and detecting a phenylhydrazine content in a 3-methyl-1-phenyl-2-pyrazolin-5-one active pharmaceutical ingredient based on the first measured value and second measured value. The first acidic water includes hydrochloric acid, the first water-soluble organic solvent is acetonitrile and/or methanol, the second acidic water includes hydrochloric acid, and the second water-soluble organic solvent is acetonitrile and/or methanol.

20 Claims, 4 Drawing Sheets

(56) References Cited

OTHER PUBLICATIONS

Extended European Search Report issued Oct. 28, 2021 in corresponding European Patent Application No. 19760101.6, 8 pages.

Tanaka et al. J. Clin. Biochem. Nutr., Nov. 2017, vol. 61, No. 3, pp. 164-168 (Published Online Oct. 26, 2017) (Year: 2017).

CN 103454370 Machine English Translation (Originally Published in Chinese on Dec. 18, 2013) (Machine Translated on Aug. 10, 2022: 7 pages) (Year: 2013).

Office Action issued Nov. 7, 2022, in corresponding Chinese Patent Application No. 201980015705.1, 16 pages.

"FDA approved edaravone for the treatment of patients with amyotrophic lateral sclerosis", Chin J of Clinical Rational Drug Use, May 2017, vol. 10 No. 5B, p. 106 (with English Translation).

Office Action issued Mar. 22, 2023 in corresponding Japanese Patent Application No. 2020-503541 (with machine-generated English Translation), 15 pages.

\* cited by examiner

ANALYSIS METHOD OF 3-METHYL-1-PHENYL-2-PYRAZOLIN-5-ONE ACTIVE PHARMACEUTICAL INGREDIENT, TREATMENT FOR AMYOTROPHIC LATERAL SCLEROSIS, INHIBITION OF PROGRESSION OF AMYOTROPHIC LATERAL SCLEROSIS, AND METHOD OF PRODUCING MEDICAMENT CONTAINING 3-METHYL-1-PHENYL-2-PYRAZOLIN-5-ONE ACTIVE PHARMACEUTICAL INGREDIENT

CROSS-REFERENCE TO RELATED APPLICATIONS

The present application is a continuation of Ser. No. 17/730,853, filed Apr. 27, 2022, which is a divisional of U.S. application Ser. No. 17/536,947, filed Nov. 29, 2021, now abandoned, which is a continuation of U.S. application Ser. No. 16/976,287, filed Aug. 27, 2020, which is a National Stage of International Application No. PCT/JP2019/007415, filed Feb. 27, 2019, which is based upon and claims the benefit of priority to International Application No. PCT/JP2018/007544, filed Feb. 28, 2018. The present application claims the benefit of priority to U.S. application Ser. Nos. 17/730,853, 17/536,947, 16/976,287, and to International Applications No. PCT/JP2019/007415 and PCT/JP2018/007544. The entire contents of these applications are incorporated herein by reference.

BACKGROUND OF THE INVENTION

Field of the Invention

The present invention is related to a method of analyzing a 3-methyl-1-phenyl-2-pyrazolin-5-one active pharmaceutical ingredient, treatment for amyotrophic lateral sclerosis (hereinafter, may be also referred to as ALS) and inhibition of progression of ALS, and a method of producing a medicament containing a 3-methyl-1-phenyl-2-pyrazolin-5-one active pharmaceutical ingredient.

Description of Background Art

ALS, which is one of the motor neuron diseases, is an incurable disease that manifests initial symptoms such as weakness of the hands, dyskinesia of the fingers and fiber spasm of the upper limbs, and causes respiratory failure through muscle atrophy/muscular weakness, bulbar paralysis and muscle fiber spasm. ALS is classified into upper limb type, bulbar type, lower limb type and mixed type depending on the onset site, all of which show that muscle groups of the whole body are affected while the symptoms progress. As a pharmaceutical product effective in treating ALS and suppressing progress of ALS, the medicaments that contains a 3-methyl-1-phenyl-2-pyrazolin-5-one active pharmaceutical ingredient have been approved and clinically used in Japan, the United States, and so on (for example, generic name "edaravone", brand names "Radicut (registered trademark)", "Radicava (registered trademark)" manufactured and sold by Mitsubishi Tanabe Pharma Corporation).

The medicaments may contain phenylhydrazine as one of the impurities. As a method of analyzing phenylhydrazine contained in 3-methyl-1-phenyl-2-pyrazolin-5-one, the method has been reported, which comprises preparing ammonium dihydrogen phosphate solution-methanol whose pH is adjusted to 2.0 with phosphoric acid as a liquid for dissolution, and analyzing phenylhydrazine by HPLC using the liquid for dissolution of ammonium dihydrogen phosphate solution-methanol whose pH is adjusted to 3.5 with phosphoric acid as a mobile phase (Central South Pharmacy, August 2014, Vol.12 No.8, 814-816). The entire contents of this publication are incorporated herein by reference.

SUMMARY OF THE INVENTION

According to one aspect of the present invention, a method of analyzing a phenylhydrazine content in a 3-methyl-1-phenyl-2-pyrazolin-5-one active pharmaceutical ingredient includes obtaining a first measured value by measuring a phenylhydrazine content in a phenylhydrazine standard solution including phenylhydrazine or a salt thereof, a first acidic water and a first water-soluble organic solvent and having a phenylhydrazine concentration in a range of 0.01 µg/mL to 10 µg/mL, obtaining a second measured value by measuring a phenylhydrazine content in a 3-methyl-1-phenyl-2-pyrazolin-5-one sample solution including a 3-methyl-1-phenyl-2-pyrazolin-5-one active pharmaceutical ingredient, a second acidic water and a second water-soluble organic solvent, and detecting a phenylhydrazine content in a 3-methyl-1-phenyl-2-pyrazolin-5-one active pharmaceutical ingredient based on the first measured value and the second measured value. The first acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, the first water-soluble organic solvent is at least one selected from the group consisting of acetonitrile and methanol, provided that when the first water-soluble organic solvent is methanol, the first acidic water is at least one selected from the group consisting of hydrochloric acid, an aqueous acetic acid solution, an aqueous trifluoroacetic acid solution, an aqueous formic acid solution and an aqueous perchloric acid solution, the second acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one selected from the group consisting of acetonitrile and methanol, provided that when the second water-soluble organic solvent is methanol, the second acidic water is at least one selected from the group consisting of hydrochloric acid, an aqueous acetic acid solution, an aqueous trifluoroacetic acid solution, an aqueous formic acid solution and an aqueous perchloric acid solution.

According to another aspect of the present invention, a method of treating amyotrophic lateral sclerosis includes obtaining a first measured value by measuring a phenylhydrazine content in a phenylhydrazine standard solution including phenylhydrazine or a salt thereof, a first acidic water and a first water-soluble organic solvent and having a phenylhydrazine concentration in a range of 0.01 µg/mL to 10 µg/mL, obtaining a second measured value by measuring a phenylhydrazine content in a 3-methyl-1-phenyl-2-pyrazolin-5-one sample solution including a 3-methyl-1-phenyl-2-pyrazolin-5-one active pharmaceutical ingredient, a second acidic water and a second water-soluble organic solvent, detecting a phenylhydrazine content in a 3-methyl-1-phenyl-2-pyrazolin-5-one active pharmaceutical ingredient based on a based the first measured value and the second measured value to determine whether the phenylhydrazine content in the 3-methyl-1-phenyl-2-pyrazolin-5-one active pharmaceutical ingredient is 20 ppm or less, and administering a medicament including the 3-methyl-1-phenyl-2-pyrazolin-5-one active pharmaceutical ingredient to a patient in need thereof such that the phenylhydrazine content in the 3-methyl-1-phenyl-2-pyrazolin-5-one active pharmaceutical ingredient is 20 ppm or less. The first acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, the first water-soluble organic solvent is at least one selected from the group consisting of acetonitrile and methanol, provided that when the first water-soluble organic solvent is methanol, the first acidic water is at least one selected from the group consisting of hydrochloric acid, an aqueous acetic acid solution, an aqueous trifluoroacetic acid solution, an aqueous formic acid solution and an aqueous perchloric acid solution, the second acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one selected from the group consisting of acetonitrile and methanol, provided that when the second water-soluble organic solvent is methanol, the second acidic water is at least one selected from the group consisting of hydrochloric acid, an aqueous acetic acid solution, an aqueous trifluoroacetic acid solution, an aqueous formic acid solution and an aqueous perchloric acid solution.

According to yet another aspect of the present invention, a method of suppressing progress of amyotrophic lateral sclerosis includes obtaining a first measured value by measuring a phenylhydrazine content in a phenylhydrazine standard solution including phenylhydrazine or a salt thereof, a first acidic water and a first water-soluble organic solvent and having a phenylhydrazine concentration in a range of 0.01 μg/mL to 10 μg/mL, obtaining a second measured value by measuring a phenylhydrazine content in a 3-methyl-1-phenyl-2-pyrazolin-5-one sample solution including a 3-methyl-1-phenyl-2-pyrazolin-5-one active pharmaceutical ingredient, a second acidic water and a second water-soluble organic solvent, detecting a phenylhydrazine content in a 3-methyl-1-phenyl-2-pyrazolin-5-one active pharmaceutical ingredient based on the first measured value and the second measured value to determine whether the phenylhydrazine content in the 3-methyl-1-phenyl-2-pyrazolin-5-one active pharmaceutical ingredient is 20 ppm or less, and administering a medicament including the 3-methyl-1-phenyl-2-pyrazolin-5-one active pharmaceutical ingredient to a patient in need thereof such that the phenylhydrazine content in the 3-methyl-1-phenyl-2-pyrazolin-5-one active pharmaceutical ingredient is 20 ppm or less. The first acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, the first water-soluble organic solvent is at least one selected from the group consisting of acetonitrile and methanol, provided that when the first water-soluble organic solvent is methanol, the first acidic water is at least one selected from the group consisting of hydrochloric acid, an aqueous acetic acid solution, an aqueous trifluoroacetic acid solution, an aqueous formic acid solution and an aqueous perchloric acid solution, the second acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one selected from the group consisting of acetonitrile and methanol, provided that when the second water-soluble organic solvent is methanol, the second acidic water is at least one selected from the group consisting of hydrochloric acid, an aqueous acetic acid solution, an aqueous trifluoroacetic acid solution, an aqueous formic acid solution and an aqueous perchloric acid solution.

According to still another aspect of the present invention, a medicament for treating amyotrophic lateral sclerosis or suppressing progress of amyotrophic lateral sclerosis, wherein the medicament is produced by a process including obtaining a first measured value by measuring a phenylhydrazine content in a phenylhydrazine standard solution including phenylhydrazine or a salt thereof, a first acidic water and a first water-soluble organic solvent and having a phenylhydrazine concentration in a range of 0.01 μg/mL to 10 μg/mL, obtaining a second measured value by measuring a phenylhydrazine content in a 3-methyl-1-phenyl-2-pyrazolin-5-one sample solution including a 3-methyl-1-phenyl-2-pyrazolin-5-one active pharmaceutical ingredient, a second acidic water and a second water-soluble organic solvent, detecting a phenylhydrazine content in a 3-methyl-1-phenyl-2-pyrazolin-5-one active pharmaceutical ingredient based on the first measured value and the second measured value to determine whether the phenylhydrazine content in the 3-methyl-1-phenyl-2-pyrazolin-5-one active pharmaceutical ingredient is 20 ppm or less, and mixing the 3-methyl-1-phenyl-2-pyrazolin-5-one active pharmaceutical ingredient with at least one pharmacologically and pharmaceutically acceptable additive such that the phenylhydrazine content in the 3-methyl-1-phenyl-2-pyrazolin-5-one active pharmaceutical ingredient is 20 ppm or less. The first acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the first water-soluble organic solvent is at least one selected from the group consisting of acetonitrile and methanol, provided that when the first water-soluble organic solvent is methanol, the first acidic water is at least one selected from the group consisting of hydrochloric acid, an aqueous acetic acid solution, an aqueous trifluoroacetic acid solution, an aqueous formic acid solution and an aqueous perchloric acid solution, the second acidic water is at least one selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one selected from the group consisting of acetonitrile and methanol, provided that when the second water-soluble organic solvent is methanol, the second acidic water is at least one selected from the group consisting of hydrochloric acid, an aqueous acetic acid solution, an aqueous trifluoroacetic acid solution, an aqueous formic acid solution and an aqueous perchloric acid solution.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
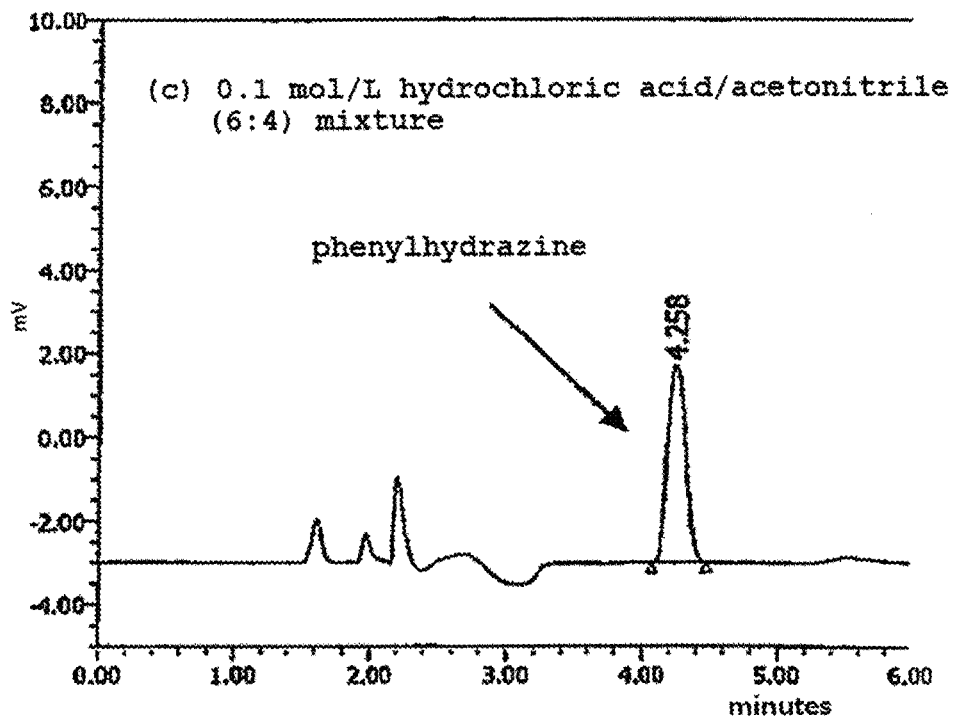
FIG. 1 is an HPLC chromatogram of a phenylhydrazine solution prepared with a 0.1 mol/L hydrochloric acid/acetonitrile (6:4) mixture.
Figure 2:
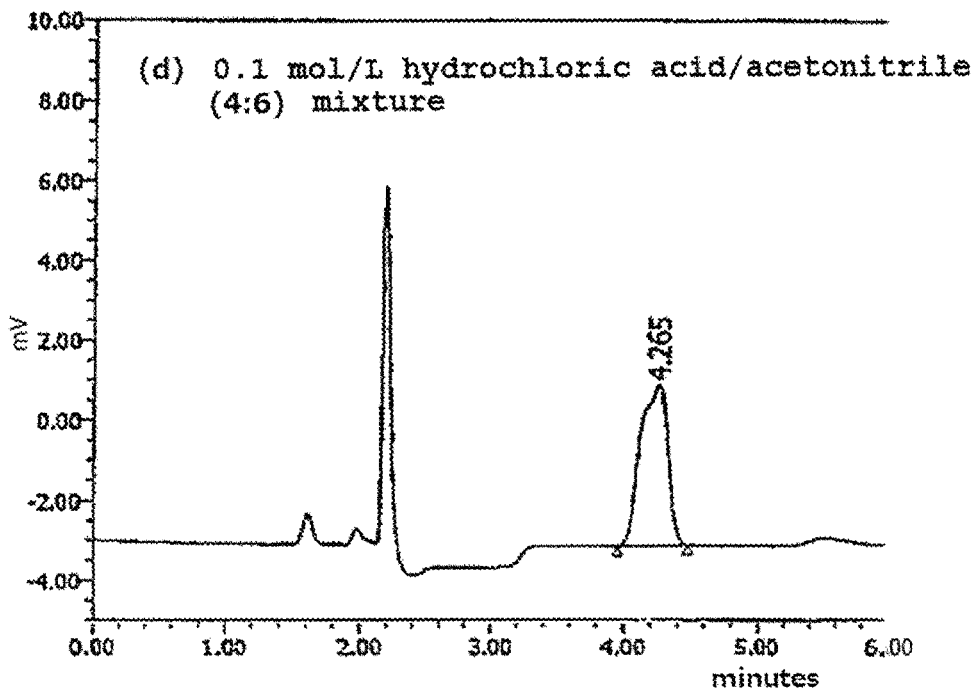
FIG. 2 is an HPLC chromatogram of a phenylhydrazine solution prepared with a 0.1 mol/L hydrochloric acid/acetonitrile (4:6) mixture.
Figure 3:
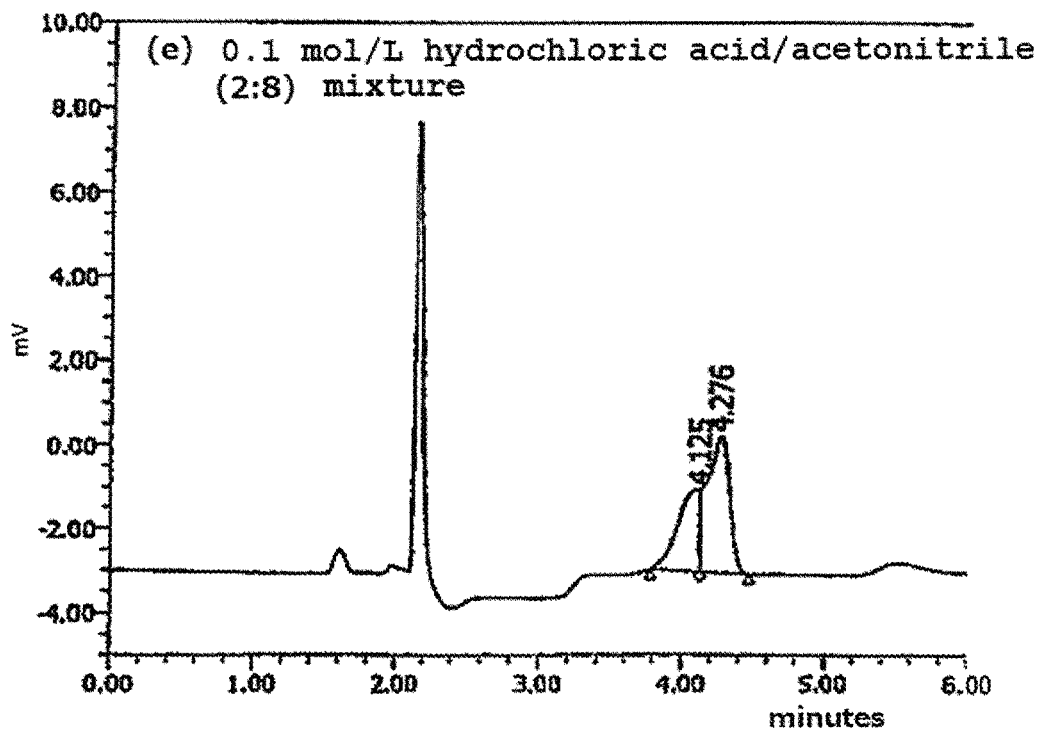
FIG. 3 is an HPLC chromatogram of a phenylhydrazine solution prepared with a 0.1 mol/L hydrochloric acid/acetonitrile (2:8) mixture.
Figure 4:
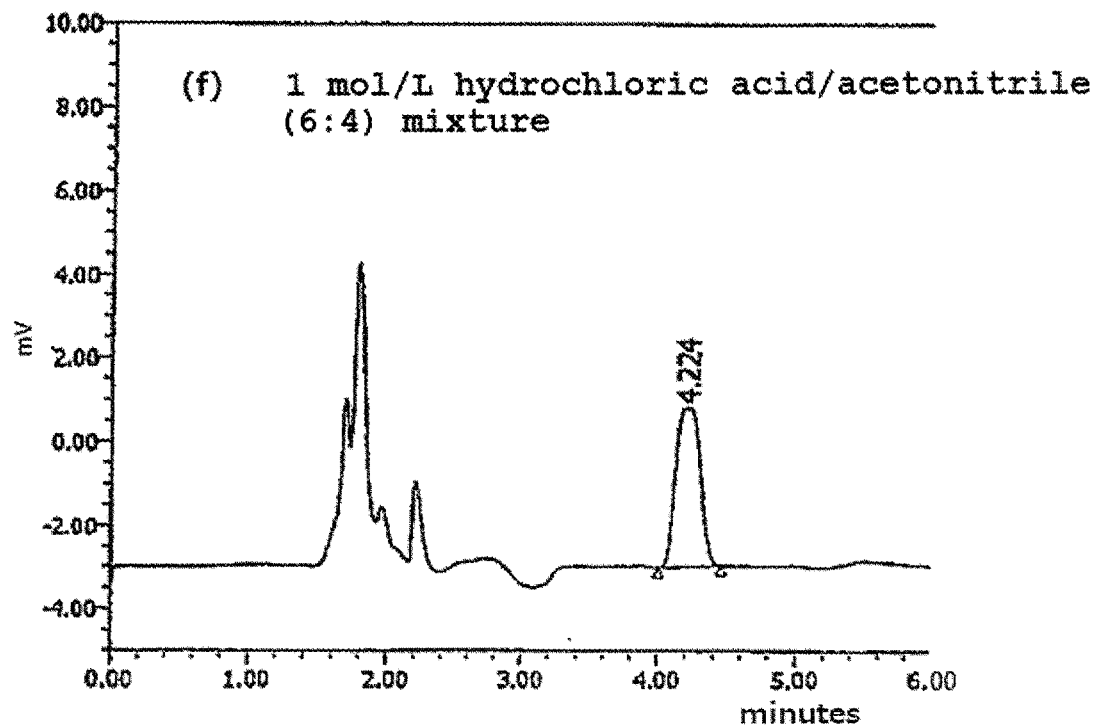
FIG. 4 is an HPLC chromatogram of a phenylhydrazine solution prepared with a 1 mol/L hydrochloric acid/acetonitrile (6:4) mixture.

Embodiments will now be described with reference to the accompanying drawings, wherein like reference numerals designate corresponding or identical elements throughout the various drawings.

Embodiments of a method of analyzing a 3-methyl-1-phenyl-2-pyrazolin-5-one active pharmaceutical ingredient, a method of treating amyotrophic lateral sclerosis (hereinafter, may be also referred to as ALS), a method of suppressing progress of amyotrophic lateral sclerosis, and a method of producing a medicament containing a 3-methyl-1-phenyl-2-pyrazolin-5-one active pharmaceutical ingredient are described in detail hereinafter, with reference to the accompanying drawings.

A method of analyzing the phenylhydrazine content in a 3-methyl-1-phenyl-2-pyrazolin-5-one active pharmaceutical ingredient according to the present invention comprises obtaining a first measured value by measuring the phenylhydrazine content in a phenylhydrazine standard solution that contains phenylhydrazine or a salt thereof, a first acidic water and a first water-soluble organic solvent and that exhibits a phenylhydrazine concentration of 0.01 μg/mL to 10 μg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, and detecting the phenylhydrazine content in the 3-methyl-1-phenyl-2-pyrazolin-5-one active pharmaceutical ingredient on the basis of the first measured value and the second measured value.

The method of analyzing the phenylhydrazine content in a 3-methyl-1-phenyl-2-pyrazolin-5-one active pharmaceutical ingredient according to the present invention may further comprise other steps, if necessary. 3-Methyl-1-phenyl-2-pyrazolin-5-one may be represented by the following structural formula. As for 3-methyl-1-phenyl-2-pyrazolin-5-one, the tautomers represented by the following structural formulas exist.

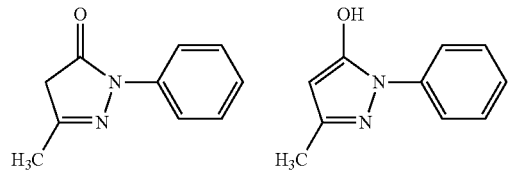

The phenylhydrazine content in a 3-methyl-1-phenyl-2-pyrazolin-5-one active pharmaceutical ingredient can be determined by analyzing a sample solution of a 3-methyl-1-phenyl-2-pyrazolin-5-one active pharmaceutical ingredient through one or more of the quantitative analytical techniques, and comparing the resultant test result with the test result obtained in a standard solution of a substantially pure phenylhydrazine.

It is preferable that a sample solution of a 3-methyl-1-phenyl-2-pyrazolin-5-one active pharmaceutical ingredient and a standard solution of phenylhydrazine should be ones in which a 3-methyl-1-phenyl-2-pyrazolin-5-one active pharmaceutical ingredient and phenylhydrazine or a salt thereof are completely dissolved in a solvent used therefor. Use of such a solution enables to measure the accurate content of phenylhydrazine contained in a 3-methyl-1-phenyl-2-pyrazolin-5-one active pharmaceutical ingredient.

It can be visually confirmed whether or not a 3-methyl-1-phenyl-2-pyrazolin-5-one active pharmaceutical ingredient and phenylhydrazine or a salt thereof are completely dissolved. An undissolved residue in minute amounts would be checked by evaluating the same filtered with a filter followed by measuring with HPLC.

It is desirable that, in a sample solution of a 3-methyl-1-phenyl-2-pyrazolin-5-one active pharmaceutical ingredient and a standard solution of phenylhydrazine, 3-methyl-1-phenyl-2-pyrazolin-5-one or a physiologically acceptable salt thereof and/or phenylhydrazine would not substantially decompose until each solution is prepared and then analyzed after a certain period of time. Phenylhydrazine can be exemplified as one of the decomposition products of 3-methyl-1-phenyl-2-pyrazolin-5-one or a physiologically acceptable salt thereof, and the degree of decomposition of 3-methyl-1-phenyl-2-pyrazolin-5-one or a physiologically acceptable salt thereof can be checked by determining the change in the phenylhydrazine content in the solution. The phenylhydrazine content in a sample solution of a 3-methyl-1-phenyl-2-pyrazolin-5-one active pharmaceutical ingredient and/or a standard solution of phenylhydrazine can be measured by analysis method using HPLC as described below.

Regarding the description that phenylhydrazine would not substantially decompose, specifically the value measured after a certain period of time does not change preferably by 20% or more, more preferably it does not change by 10% or more, and even more preferably it does not change by 5% or more, compared with the value of phenylhydrazine measured within 30 minutes after preparing a phenylhydrazine standard solution.

Further, regarding the description that 3-methyl-1-phenyl-2-pyrazolin-5-one or a physiologically acceptable salt thereof would not substantially decompose, specifically the value of phenylhydrazine measured after a certain period of time does not change preferably by 4 ppm or more relative to the content of 3-methyl-1-phenyl-2-pyrazolin-5-one, more preferably, it does not change by 2 ppm or more, and even more preferably, it does not change by 1 ppm or more, compared with the value of phenylhydrazine measured within 30 minutes after preparing a sample solution of a 3-methyl-1-phenyl-2-pyrazolin-5-one active pharmaceutical ingredient.

A certain period of time is not particularly limited. Preferably it is 2 hours, 3 hours, 4 hours, 5 hours, 9 hours, 10 hours, 12 hours or 24 hours, more preferably it is 2 hours, 3 hours, 4 hours, 5 hours, 9 hours, 10 hours or 12 hours, and it is even more preferably 2 hours, 3 hours, 4 hours or 5 hours.

A sample solution of a 3-methyl-1-phenyl-2-pyrazolin-5-one active pharmaceutical ingredient contains a 3-methyl-1-phenyl-2-pyrazolin-5-one active pharmaceutical ingredient, an acidic water, and a water-soluble organic solvent.

The acidic water is at least one type selected from the group consisting of hydrochloric acid, an aqueous acetic acid solution, an aqueous trifluoroacetic acid solution, an aqueous formic acid solution, an aqueous phosphoric acid solution, and an aqueous perchloric acid solution. These acidic waters may be used alone, or a mixture prepared by mixing two or more acidic waters at an appropriate ratio may be used. At least one type selected from the group consisting of hydrochloric acid, an aqueous acetic acid solution, an aqueous trifluoroacetic acid solution and an aqueous formic acid solution is preferable, and hydrochloric acid is more preferable.

The acid concentration of the acidic water is preferably 0.01 mol/L to 5 mol/L, more preferably 0.02 mol/L to 1 mol/L, and even more preferably 0.05 mol/L to 0.2 mol/L, and even more preferably 0.1 mol/L.

The water-soluble organic solvent is at least one type selected from the group consisting of acetonitrile and methanol. These water-soluble organic solvents may be used alone, or a mixture prepared by mixing these solvents at an appropriate ratio may be used. Acetonitrile is preferable.

When the water-soluble organic solvent is methanol, the acidic water is at least one type selected from the group consisting of hydrochloric acid, an aqueous acetic acid solution, an aqueous trifluoroacetic acid solution, an aqueous formic acid solution and an aqueous perchloric acid solution.

The ratio of the acidic water and the water-soluble organic solvent can be changed appropriately. The volume ratio of acidic water:water-soluble organic solvent can be 3:1 to 4:5, preferably 3:1 to 5:5, and more preferably 3:1 to 6:4. For example, the volume ratio of acidic water:water-soluble organic solvent can be 7:3, 6:4, and 5:5. When the acidic water and the water-soluble organic solvent are hydrochloric acid and acetonitrile, respectively, a particularly preferable volume ratio is 7:3. When the acidic water and the water-soluble organic solvent are hydrochloric acid and methanol, respectively, a particularly preferable volume ratio is 5:5.

A method of preparing a sample solution is not particularly limited as long as the sample solution contains a 3-methyl-1-phenyl-2-pyrazolin-5-one active pharmaceutical ingredient, an acidic water and a water-soluble organic solvent. An acidic water prepared may be mixed with a 3-methyl-1-phenyl-2-pyrazolin-5-one active pharmaceutical ingredient and a water-soluble organic solvent to prepare a sample solution, and further, a water may be mixed with a 3-methyl-1-phenyl-2-pyrazolin-5-one active pharmaceutical ingredient and/or a water-soluble organic solvent, followed by adding a corresponding acid to the mixture to prepare a sample solution.

A standard solution of phenylhydrazine contains phenylhydrazine or a salt thereof, an acidic water, and a water-soluble organic solvent.

The phenylhydrazine standard solution may further contain a 3-methyl-1-phenyl-2-pyrazolin-5-one active pharmaceutical ingredient.

Examples of the salt of phenylhydrazine include salts with mineral acids such as hydrochloric acid, sulfuric acid, hydrobromic acid and phosphoric acid. As the phenylhydrazine or a salt thereof, a salt of phenylhydrazine is preferable. As the salt of phenylhydrazine, phenylhydrazine hydrochloride is preferable.

According to the analysis method of the present invention, phenylhydrazine hydrochloride is more preferable than phenylhydrazine as the former is less likely to be decomposed during storage, and therefore is most preferable as phenylhydrazine or a salt thereof used in the standard solution of the present invention.

It is desirable that phenylhydrazine or a salt thereof would be substantially pure. Specifically, the purity is preferably at least 90% or more, more preferably at least 95% or more, at least 98% or more, and even more preferably at least 99% or more. Phenylhydrazine hydrochloride having a purity of 98% or more and a purity of 99% or more is commercially available (for example, phenylhydrazine hydrochloride, 99%; Alfa Aesar; code: A14645), and such a commercially available product may be used.

The acidic water is at least one type selected from the group consisting of hydrochloric acid, an aqueous acetic acid solution, an aqueous trifluoroacetic acid solution, an aqueous formic acid solution, an aqueous phosphoric acid solution, and an aqueous perchloric acid solution. These acidic waters may be used alone, or a mixture prepared by mixing two or more acidic waters at an appropriate ratio may be used. At least one type selected from the group consisting of hydrochloric acid, an aqueous acetic acid solution, an aqueous trifluoroacetic acid solution and an aqueous formic acid solution is preferable, and hydrochloric acid is more preferable.

The acid concentration of the acidic water is preferably 0.01 mol/L to 5 mol/L, more preferably 0.02 mol/L to 1 mol/L, and even more preferably 0.05 mol/L to 0.2 mol/L. And even more preferably 0.1 mol/L.

The water-soluble organic solvent is at least one type selected from the group consisting of acetonitrile and methanol. These water-soluble organic solvents may be used alone, or a mixture prepared by mixing these solvents at an appropriate ratio may be used. Acetonitrile is preferable.

When the water-soluble organic solvent is methanol, the acidic water is at least one type selected from the group consisting of hydrochloric acid, an aqueous acetic acid solution, an aqueous trifluoroacetic acid solution, an aqueous formic acid solution and an aqueous perchloric acid solution. The concentration of phenylhydrazine in a phenylhydrazine standard solution can be appropriately adjusted according to the concentration of phenylhydrazine in a 3-methyl-1-phenyl-2-pyrazolin-5-one active pharmaceutical ingredient to be analyzed.

For example, the concentration of phenylhydrazine in a phenylhydrazine standard solution (the concentration of phenylhydrazine in the case of a phenylhydrazine free form, and the concentration equivalent to phenylhydrazine in the case of a salt of phenylhydrazine) may be adjusted from 0.01 μg/mL to 10 μg/mL, preferably 0.05 μg/mL to 2 μg/mL, and more preferably 0.1 μg/mL to 1 μg/mL.

Alternatively, the concentration of phenylhydrazine in a phenylhydrazine standard solution can be adjusted to a concentration equivalent to 1 ppm to 200 ppm corresponding to the dilution ratio of a sample solution of a 3-methyl-1-phenyl-2-pyrazolin-5-one active pharmaceutical ingredient. The concentration equivalent to ppm means a concentration corresponding to the dilution ratio of a sample solution of a 3-methyl-1-phenyl-2-pyrazolin-5-one active pharmaceutical ingredient. For example, when 0.10 g of 3-methyl-1-phenyl-2-pyrazolin-5-one is mixed with an acidic water and a water-soluble organic solvent to make 10 mL, the concentration equivalent to 1 ppm is 0.01 μg/mL. The concentration equivalent to 5 ppm to 100 ppm is preferable, and the concentration equivalent to 10 ppm to 50 ppm is more preferable.

An embodiment of the present invention comprises obtaining a first measured value by measuring the phenylhydrazine content of a phenylhydrazine standard solution that exhibits a phenylhydrazine concentration of 0.01 μg/mL to 10 μg/mL. The number of the first measured value is not particularly limited as long as it can be compared with a second measured value obtained by measuring the phenylhydrazine content in a 3-methyl-1-phenyl-2-pyrazolin-5-one sample solution, which number can be one or more.

The ratio of the acidic water and the water-soluble organic solvent can be changed appropriately. The volume ratio of acidic water:water-soluble organic solvent can be 3:1 to 4:5, preferably 3:1 to 5:5, and more preferably 3:1 to 6:4. For example, the volume ratio of acidic water:water-soluble organic solvent can be 7:3, 6:4, and 5:5. Particularly preferred is 7:3. When the acidic water and the water-soluble organic solvent are hydrochloric acid and acetonitrile, respectively, a particularly preferable volume ratio is 7:3. When the acidic water and the water-soluble organic solvent are hydrochloric acid and methanol, respectively, a particularly preferable volume ratio is 5:5.

As long as a phenylhydrazine standard solution contains phenylhydrazine or a salt thereof, an acidic water, and a water-soluble organic solvent, the method of preparing the phenylhydrazine standard solution is not particularly limited. The acidic water prepared may be mixed with phenylhydrazine or a salt thereof and a water-soluble organic solvent to prepare a phenylhydrazine standard solution, and further, water may be mixed with phenylhydrazine or a salt thereof and/or a water-soluble organic solvent, followed by adding a corresponding acid to the mixture to prepare a phenylhydrazine standard solution.

An acidic water in a sample solution of a 3-methyl-1-phenyl-2-pyrazolin-5-one active pharmaceutical ingredient is preferably the same as an acidic water in a phenylhydrazine standard solution. A water-soluble organic solvent in a sample solution of a 3-methyl-1-phenyl-2-pyrazolin-5-one active pharmaceutical ingredient is preferably the same as a water-soluble organic solvent in a phenylhydrazine standard solution. A volume ratio of acidic water to water-soluble organic solvent in a sample solution of a 3-methyl-1-phenyl-2-pyrazolin-5-one active pharmaceutical ingredient is preferably the same as a volume ratio of acidic water to water-soluble organic solvent in a phenylhydrazine standard solution.

More preferably, an acidic water, a water-soluble organic solvent and a volume ratio of the acidic water to the water-soluble organic solvent in a sample solution of a 3-methyl-1-phenyl-2-pyrazolin-5-one active pharmaceutical ingredient are the same, respectively, as an acidic water, a water-soluble organic solvent and a volume ration of the acidic water to the water-soluble organic solvent in a phenylhydrazine standard solution.

Quantitative analysis techniques include high performance liquid chromatography (HPLC). High performance liquid chromatography includes high performance liquid chromatography (HPLC) and ultrahigh performance liquid chromatography (UHPLC). When high performance liquid chromatography is used, the theoretical plate number of the phenylhydrazine peak is preferably as large as possible, and for example, the theoretical plate number N determined by the half-width method can be 1000 plates or more, and more preferably 3000 plates or more.

$$\text{Theoretical plate number: } N = 5.54 \times (tr/W_{0.5})^2 \quad \text{Formula 1}$$

where
tr: retention time, and
$W_{0.5}$: Width of half peak height

Symmetry coefficient S is an index representing the degree of symmetry of the peak on the chromatogram, and the closer the symmetry coefficient S is to 1, the more symmetrical the peak is (normal distribution). The closer the symmetry coefficient S is to 1, the higher the performances as analysis method such as accuracy, precision and limit of quantification, becomes, which is preferable. For example, symmetry coefficient S may be 2.0 or less, and more preferably 1.5 or less.

$$\text{Symmetry factor: } S = W_{0.05h}/2f \quad \text{Formula 2}$$

where
$W_{0.05h}$: Peak width at a height of 1/20 of the peak height from the peak baseline
2f: Distance on the rising side of the peak width of $W_{0.05h}$ obtained by dividing the peak width by a perpendicular line drawn from the peak top to the horizontal axis.

Examples of physiologically acceptable salts of 3-methyl-1-phenyl-2-pyrazolin-5-one or a physiologically acceptable salt thereof include salts with mineral acids such as hydrochloric acid, sulfuric acid, hydrobromic acid, phosphoric acid and the like; salts with organic acids such as methanesulfonic acid, p-toluenesulfonic acid, acetic acid, oxalic acid, citric acid, malic acid, fumaric acid and the like; salts with alkali metals such as sodium, potassium and the like; salts with alkaline earth metals such as magnesium, and the like; and salts with amines such as ammonium, ethanolamine, 2-amino-2-methyl-1-propanol and the like. Physiologically acceptable salts also include hydrates and solvates.

3-Methyl-1-phenyl-2-pyrazolin-5-one active pharmaceutical ingredient means 3-methyl-1-phenyl-2-pyrazolin-5-one or its physiologically acceptable salt as the active ingredient. A 3-methyl-1-phenyl-2-pyrazolin-5-one active pharmaceutical ingredient may contain phenylhydrazine as one of the impurities. According to the preparation method described in European Patent Publication No. 208874 (or Japanese Patent Publication (Kokoku) No. H5-31523), phenylhydrazine is used as a precursor for synthesizing 3-methyl-1-phenyl-2-pyrazolin-5-one.

A solution preparation containing a 3-methyl-1-phenyl-2-pyrazolin-5-one active pharmaceutical ingredient is prone to increase in phenylhydrazine during the storage. Phenylhydrazine is a mutagenic compound, and its exposure limit for industrial health is set in each country. The United States has legislated the strictest exposure limit for phenylhydrazine, which is 2,860 μg/kg/year. Phenylhydrazine is easily decomposed by light and oxygen.

It is preferable that the amount of impurity phenylhydrazine contained in a 3-methyl-1-phenyl-2-pyrazolin-5-one active pharmaceutical ingredient is as small as possible. For example, it is preferably 20 ppm or less, and more preferably 10 ppm or less.

When 3-methyl-1-phenyl-2-pyrazolin-5-one is used for the purpose of treating ALS or suppressing progress of ALS, it is preferable to continue the pharmacotherapy with this medicament for a lifetime starting administration of the medicament. Therefore, it is preferable that the phenylhydrazine content should be strictly controlled.

An embodiment of the present invention is a method of producing a 3-methyl-1-phenyl-2-pyrazolin-5-one active pharmaceutical ingredient having a phenylhydrazine content of 20 ppm or less, which includes: obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 µg/mL to 10 µg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, and detecting the phenylhydrazine content in the 3-methyl-1-phenyl-2-pyrazolin-5-one active pharmaceutical ingredient on the basis of the first measured value and the second measured value, to determine that the phenylhydrazine content is 20 ppm or less. The first acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the first water-soluble organic solvent is at least one type selected from the group consisting of acetonitrile and methanol, provided that, when the first water-soluble organic solvent is methanol, the first acidic water is at least one type selected from the group consisting of hydrochloric acid, an aqueous acetic acid solution, an aqueous trifluoroacetic acid solution, an aqueous formic acid solution and an aqueous perchloric acid solution, and the second acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one type selected from the group consisting of acetonitrile and methanol, provided that, when the second water-soluble organic solvent is methanol, the second acidic water is at least one type selected from the group consisting of hydrochloric acid, an aqueous acetic acid solution, an aqueous trifluoroacetic acid solution, an aqueous formic acid solution and an aqueous perchloric acid solution.

A medicament according to an embodiment of the present invention is a medicament for treating amyotrophic lateral sclerosis or suppressing progress of amyotrophic lateral sclerosis, which contains a 3-methyl-1-phenyl-2-pyrazolin-5-one active pharmaceutical ingredient wherein the phenylhydrazine content in the active pharmaceutical ingredient is 20 ppm or less, and which is produced by a method of production according to the present invention.

A medicament according to a further embodiment of the present invention contains a 3-methyl-1-phenyl-2-pyrazolin-5-one active pharmaceutical ingredient for treating amyotrophic lateral sclerosis or suppressing disease progression, which active pharmaceutical ingredient is analyzed for the phenylhydrazine content therein to determine that the phenylhydrazine content is 20 ppm or less.

In addition, the medicament may contain a 3-methyl-1-phenyl-2-pyrazolin-5-one active pharmaceutical ingredient, and a pharmacologically and pharmaceutically acceptable additive, and further may contain one or more active pharmaceutical ingredients other than the 3-methyl-1-phenyl-2-pyrazolin-5-one active pharmaceutical ingredient.

A medicament containing a pharmacologically and pharmaceutically acceptable additive according to an embodiment of the present invention may be produced by a method of production which includes mixing a 3-methyl-1-phenyl-2-pyrazoline-5-one active pharmaceutical ingredient having a phenylhydrazine content of 20 ppm or less with a pharmacologically and pharmaceutically acceptable additive.

Although an active ingredient according to an embodiment of the present invention, 3-methyl-1-phenyl-2-pyrazolin-5-one or a physiologically acceptable salt thereof, may be administered to a patient solely, it is preferable that the active ingredient would be administered in a form of a medicament as described above, which is prepared by adding a pharmacologically and pharmaceutically acceptable additive.

As a pharmacologically and pharmaceutically acceptable additive, the followings may be used: for example, an excipient, a disintegrating agent or disintegrating accelerator, a binder, a lubricant, a coating agent, a dye, a diluent, a base, a solubilizing agent or solubilizing accelerator, an isotonizing agent, a pH adjusting agent, a stabilizer, a propellant, an adhesive agent and the like. Examples of dosage forms suitable for oral administration include, for example, a tablet, a capsule, a powder, a fine granule, a granule, a liquid, a syrup and the like, and examples of dosage forms suitable for parenteral administration include an injection, a drip infusion, a patch, a suppository and the like.

As an additive in the medicament suitable for oral administration, the followings may be used: for example, excipients such as glucose, lactose, D-mannitol, starch or crystalline cellulose; disintegrating agents or disintegrating accelerators such as carboxymethylcellulose, starch, or carboxymethylcellulose calcium; binders such as hydroxypropylcellulose, hydroxypropylmethylcellulose, polyvinylpyrrolidone or gelatin; lubricants such as magnesium stearate or talc; coating agents such as hydroxypropylmethylcellulose, sucrose, polyethylene glycol or titanium oxide; and bases such as petroleum jelly, liquid paraffin, polyethylene glycol, gelatin, kaolin, glycerin, purified water, or hard fat.

As a pharmaceutical additive in a medicament suitable for injection or drip infusion, the followings may be used: solubilizing agents or solubilizing accelerators that can constitute an aqueous or in-use dissolution type injection such as distilled water for injection, physiological saline, and propylene glycol; isotonizing agents such as glucose, sodium chloride, D-mannitol, and glycerin; and pH adjusting agents such as an inorganic acid, an organic acid, an inorganic base or an organic base.

Generic name "edaravone", brand name "Radicat (registered trademark)", or "Radicava (registered trademark)" manufactured and sold by Mitsubishi Tanabe Pharma Corporation, and so on, which has been already clinically used as a cerebral protective agent and a treating agent for ALS and a suppressing agent for progress of ALS containing 3-methyl-1-phenyl-2-pyrazolin-5-one as an active ingredient, may be utilized as 3-methyl-1-phenyl-2-pyrazolin-5- one or a physiologically acceptable salt thereof used in a medicament and a method according to the present invention.

A method of treating amyotrophic lateral sclerosis or suppressing the disease progression according to an embodiment of the present invention, includes administering a medicament containing an effective amount of a 3-methyl-1-phenyl-2-pyrazolin-5-one active pharmaceutical ingredient to a patient in need of the treatment or the suppression of the disease progression, wherein the 3-methyl-1-phenyl-2-pyrazolin-5-one active pharmaceutical ingredient in the medicament has a phenylhydrazine content of 20 ppm or less as a result of the analysis of the phenylhydrazine content in the 3-methyl-1-phenyl-2-pyrazolin-5-one active pharmaceutical ingredient.

This embodiment may further include obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 µg/mL to 10 µg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, and detecting the phenylhydrazine content in the 3-methyl-1-phenyl-2-pyrazolin-5-one active pharmaceutical ingredient on the basis of the first measured value and the second measured value to determine that the phenylhydrazine content is 20 ppm or less.

A method of treating amyotrophic lateral sclerosis or suppressing progress of amyotrophic lateral sclerosis according to an embodiment of the present invention may include providing a rest period during a pharmacotherapy period, setting a dosing period and a rest period as one (1) unit, thereby repeating the unit. For example, a rest period of 14 days is provided twice or more during a pharmacotherapy period, a dosing period and a rest period is set as one unit, and the unit is repeated twice or more. For example, two repeats of a dosing period and a rest period mean "dosing period, rest period, dosing period, and rest period", but the last rest period may be omitted to imply "dosing period, rest period, and dosing period".

A rest period means a period in which no medicament is administered continuously for example 7 days or more.

A dosing period may be for example 14 days, or 10 days out of 14 days. Ten days out of 14 days means any 10 days out of 14 consecutive days, and the 10 days to be administered may be 10 consecutive days or 10 inconsecutive days intervened by 1 to 4 days of a rest period. It may be 10 consecutive days that are separated by. A dosing period may be determined to be a preferred period while observing the patient's condition. A rest period in an embodiment of the present invention is preferably 14 days.

The number of repeat in the case of repeating 14-days dosing period and 14-days rest period is not particularly limited as long as it is 2 or more.

When a 14-days initial dosing period is followed by a 14-days initial rest period, and then a 10-days dosing period out of 14 days and a 14-days rest period are repeated, the number of repeat of a 10-day dosing period out of 14 days and a 14-days rest period is not particularly limited as long as it is once or more. In other embodiments, daily or near daily dosing may be repeated without any rest period.

The daily dose of the active ingredient can be appropriately selected depending on conditions such as the age and status of a patient. In general, the dose of 3-methyl-1-phenyl-2-pyrazolin-5-one (when the active ingredient is 3-methyl-1-phenyl-2-pyrazolin-5-one, the dose is the dose of 3-methyl-1-phenyl-2-pyrazolin-5-one, or when the active ingredient is a physiologically acceptable salt of 3-methyl-1-phenyl-2-pyrazolin-5-one, the dose is the dose equivalent to 3-methyl-1-Phenyl-2-pyrazolin-5-one, this is the same as below) for adults, is preferably about 15 mg to about 240 mg, more preferably about 30 mg to about 180 mg, and even more preferably about 60 mg to about 120 mg, particularly even more preferably being about 60 mg.

When the administration is repeated daily or almost daily without any rest period, in general, the daily dose of 3-methyl-1-phenyl-2-pyrazolin-5-one for adults is preferably about 60 mg, about 120 mg or about 180 mg, and more preferably about 60 mg or about 120 mg.

The number of administration per day during the dosing period is not limited, and may be selected while observing the patient's status. However, considering the burden on the patient and the like, the number is preferably three times, twice or once, and more preferably once.

The administration route of the active ingredient is not particularly limited, and the active ingredient may be administered orally or parenterally. Further, the active ingredient may be administered by bolus dosing and continuous dosing, and continuous dosing is preferable. Examples of continuous dosing include intravenous dosing by drip infusion, transdermal dosing, oral dosing using sublingual tablets, and oral and rectal dosing using sustained-release formulation, and intravenous dosing by drip infusion is preferable. In the case of bolus dosing by injection or intravenous dosing by drip infusion, for example, the injections described in JPA63-132833 and JPA2011-62529 may be used. These disclosures are incorporated herein by reference.

In the case of intravenous dosing by drip infusion, the dosing rate is preferably about 0.5 mg/min to about 1 mg/min for the amount of 3-methyl-1-phenyl-2-pyrazolin-5-one, which is about 15 minutes to about 480 minutes in terms of time, being preferably about 30 minutes to about 120 minutes, more preferably about 30 minutes to about 60 minutes, and even more preferably about 60 minutes.

Other dosage forms include a dosage form that is substantially equivalent to the intravenous dosing by drip infusion at a dose of about 0.5 mg to about 1 mg of 3-methyl-1-phenyl-2-pyrazolin-5-one per minute. The dosage form that is substantially equivalent to the intravenous dosing by drip infusion at a dose of about 0.5 mg to about 1 mg of 3-methyl-1-phenyl-2-pyrazolin-5-one per minute may be substantially equivalent to the intravenous dosing in view of pharmacokinetics. A specific example of the dosage form is a dosage form in which the time-dependent changes in the concentration of the unchanged 3-methyl-1-phenyl-2-pyrazolin-5 in plasma after the administration of 3-methyl-1-phenyl-2-pyrazolin-5-one or a physiologically acceptable salt thereof is confirmed to be substantially equivalent to the intravenous dosing. Examples of such dosing forms include transdermal dosing, oral dosing using sublingual tablets, and oral and rectal dosing using sustained-release formulations, and the like.

A method of analyzing the phenylhydrazine content in a 3-methyl-1-phenyl-2-pyrazolin-5-one active pharmaceutical ingredient according to an embodiment of the present invention may include preparing a phenylhydrazine standard solution that contains phenylhydrazine or a salt thereof, a first acidic water and a water-soluble organic solvent; and/or preparing a 3-methyl-1-phenyl-2-pyrazolin-5-one sample solution that contains a 3-methyl-1-phenyl-2-pyrazolin-5- one active pharmaceutical ingredient, a second acidic water and a second water-soluble organic solvent.

In accordance with a method of analyzing the phenylhydrazine content in a 3-methyl-1-phenyl-2-pyrazolin-5-one active pharmaceutical ingredient according to another embodiment of the present invention, the first measured value of phenylhydrazine is a value obtained by measuring a phenylhydrazine standard solution using high performance liquid chromatography, and/or the second measured value of phenylhydrazine is a value obtained by measuring a 3-methyl-1-phenyl-2-pyrazolin-5-one sample solution using high performance liquid chromatography.

A method of treating amyotrophic lateral sclerosis or suppressing progress of amyotrophic lateral sclerosis according to another embodiment of the present invention includes administering a medicament containing an effective amount of a 3-methyl-1-phenyl-2-pyrazolin-5-one active pharmaceutical ingredient to a patient in need thereof. The 3-methyl-1-phenyl-2-pyrazolin-5-one active pharmaceutical ingredient was a 3-methyl-1-phenyl-2-pyrazolin-5-one that is analyzed and determined that the phenylhydrazine content is 20 ppm or less. The analysis of the phenylhydrazine content comprises obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 μg/mL to 10 μg/mL, to obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, and detecting the phenylhydrazine content in the 3-methyl-1-phenyl-2-pyrazolin-5-one active pharmaceutical ingredient on the basis of the first measured value and the second measured value, to determine that the phenylhydrazine content is 20 ppm or less.

A method of producing a medicament for treating amyotrophic lateral sclerosis or suppressing progress of amyotrophic lateral sclerosis according to an embodiment of the present invention includes mixing a 3-methyl-1-phenyl-2-pyrazoline-5-one active pharmaceutical ingredient determined by analyzing a phenylhydrazine content therein to determine that the content of a phenylhydrazine content is 20 ppm or less, together with at least one pharmacologically and pharmaceutically acceptable additive. The analysis of the phenylhydrazine content comprises obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 μg/mL to 10 μg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, and detecting the phenylhydrazine content in the 3-methyl-1-phenyl-2-pyrazolin-5-one active pharmaceutical ingredient on the basis of the first measured value and the second measured value, to determine that the phenylhydrazine content is 20 ppm or less.

A medicament according to yet another embodiment of the present invention is a medicament for intravenous dosing which contains a 3-methyl-1-phenyl-2-pyrazolin-5-one active pharmaceutical ingredient having a phenylhydrazine content of 20 ppm or less.

A method of producing a medicament for treating amyotrophic lateral sclerosis or suppressing progress of amyotrophic lateral sclerosis according to an embodiment of the present invention involves at least one pharmacologically and pharmaceutically acceptable additive which is distilled water for injection, or physiological saline.

EXAMPLES

Hereinafter, embodiments of the present invention are illustrated by means of the following examples, but the present invention is not limited to them in any aspect. In those examples, 3-methyl-1-phenyl-2-pyrazolin-5-one, which is an active pharmaceutical ingredient, is referred to as an edaravone active pharmaceutical ingredient (may be also referred to as EDVP).

Test Example 1

Investigation of Liquid for Dissolution

The concentration of an acidic water, a ratio of an acidic water to a water-soluble organic solvent and so on are changed to investigate the conditions under which an edaravone active pharmaceutical ingredient and phenylhydrazine or a salt thereof can be dissolved. Further, the peak shape of phenylhydrazine is also checked by the HPLC measurement to investigate an optimum concentration of an acidic water and an optimal ratio of an acidic water to a water-soluble organic solvent.

The following liquids for dissolution (a) to (f) were used to prepare sample solutions, and the dissolution states of the edaravone active pharmaceutical ingredient in those solutions were investigated. Then, a liquid for dissolution that enabled to dissolve the edaravone active pharmaceutical ingredient was used to prepare a solution of phenylhydrazine, and the solution was measured using HPLC to check the peak shape of phenylhydrazine.

Liquids for Dissolution
 (a) 0.1 mol/L hydrochloric acid test liquid
 (b) 0.1 mol/L hydrochloric acid/acetonitrile (8:2) mixture
 (c) 0.1 mol/L hydrochloric acid/acetonitrile (6:4) mixture
 (d) 0.1 mol/L hydrochloric acid/acetonitrile (4:6) mixture
 (e) 0.1 mol/L hydrochloric acid/acetonitrile (2:8) mixture
 (f) 1 mol/L hydrochloric acid/acetonitrile (6:4) mixture Preparation of Sample Solutions The edaravone active pharmaceutical ingredient weighed to about 0.10 g was dissolved in liquids for dissolution (a) to (f), and the solutions were adjusted exactly to 10 mLs to provide sample solutions.

Preparation of Phenylhydrazine Solutions

To 5 μL of phenylhydrazine collected, 0.1 mol/L hydrochloric acid test liquid was added, followed by adjusting exactly to 100 mL. To the solution measured precisely to 0.1 ml, liquids for dissolution (a) to (f) were added, and the solutions were adjusted exactly to 10 mLs to provide phenylhydrazine solutions (0.5 μg/mL).

Test Conditions

The measurement by HPLC was performed under the conditions of the feeding liquid for mobile phase as follows.
 Mobile phase A: 0.05 mol/L aqueous sodium perchlorate solution at pH 2.5/acetonitrile (90:10) mixture
 Mobile phase B: 0.05 mol/L aqueous sodium perchlorate solution at pH 2.5/acetonitrile (10:90) mixture Feeding liquid for mobile phase: The concentration gradient was controlled by changing the mixing ratio of mobile phase A and mobile phase B as follows:

TABLE 1

| Time after injection (minutes) | Mobile phase A (vol %) | Mobile phase B (vol %) |
|---|---|---|
| 0-7 | 100 | 0 |
| 7-7.1 | 100 -> 0 | 0 -> 100 |
| 7.1-20 | 0 | 100 |

The result of each liquid for dissolution is shown in Table 2, and the chromatograms of the phenylhydrazine solutions are shown in FIGS. 1 to 4. Judging from the solubility of EDVP and the peak shape of phenylhydrazine, it was found that (c) 0.1 mol/L hydrochloric acid/acetonitrile (6:4) mixture was the most suitable, and (f) 1 mol/L hydrochloric acid/acetonitrile (6:4) mixture could also be used.

TABLE 2

Result of each liquid for dissolution

| liquids for dissolution | sample solutions | | phenylhydrazine solutions | |
|---|---|---|---|---|
| | solubility of EDVP | pH*[5] | peak shape | pH*[5] |
| (a) 0.1 mol/L hydrochloric acid test liquid | insoluble | — | — | — |
| (b) 0.1 mol/L hydrochloric acid/acetonitrile (8:2) mixture | insoluble | — | — | — |
| (c) 0.1 mol/L hydrochloric acid/acetonitrile (6:4) mixture | soluble | 2 | excellent | 1 |
| (d) 0.1 mol/L hydrochloric acid/acetonitrile (4:6) mixture | soluble | 2 | bad | 1 |
| (e) 0.1 mol/L hydrochloric acid/acetonitrile (2:8) mixture | soluble | 3 | bad | 1 |
| (f) 1 mol/L hydrochloric acid/acetonitrile (6:4) mixture | soluble | 1 | good | 1 |

*[5]Measured with pH test paper

In the test example, it was revealed that phenylhydrazine hydrochloride was less likely to decompose during storage and was easier to handle than phenylhydrazine, showing that the hydrochloride is more suitable as a standard substance.

Accordingly, in the test example, a standard solution prepared with phenylhydrazine hydrochloride was used to perform the measurement. The peak of phenylhydrazine provides a theoretical plate number and a symmetry coefficient.

In addition, according to the test example, the viewpoint of the solubility of EDVP and the peak shape of phenylhydrazine revealed that it was not possible to prepare any liquid for dissolution optimal for use in the analysis of an edaravone active pharmaceutical ingredient by merely adjusting the pH to 2.

Test Example 2

Further Investigation of Liquids for Dissolution
Since the results of Test Example 1 revealed that liquid for dissolution (c), which is 0.1 mol/L hydrochloric acid/acetonitrile (6:4) mixture, was the most suitable liquid for dissolution, liquid for dissolution (g), which is 0.1 mol/L hydrochloric acid/acetonitrile (7:3) mixture, was used to prepare a standard solution, and the comparison between the liquids for dissolution in order to obtain a more preferable peak shape of a phenylhydrazine solution.

Liquid for dissolution (c) and liquid for dissolution (g) as described below were used to prepare standard solutions, and the peak shapes of phenylhydrazine were further investigated.

Liquids for Dissolution
(c) 0.1 mol/L hydrochloric acid/acetonitrile (6:4) mixture
(g) 0.1 mol/L hydrochloric acid/acetonitrile (7:3) mixture Preparation of Standard Solutions
Phenylhydrazine hydrochloride weighed precisely to about 13.4 mg (about 10 mg as a free form) was dissolved in liquid for dissolution (c) and liquid for dissolution (g) respectively, and the solutions were adjusted exactly to 100 mLs. To the solutions measured precisely to 2 mLs, liquid for dissolution (c) and liquid for dissolution (g) were added, respectively, and the solutions were adjusted exactly to 20 mLs. To the solutions measured precisely to 2 mLs, liquids for dissolution were added, and the solutions were adjusted exactly to 20 mLs to provide standard solutions (phenylhydrazine: 1 µg/mL).

Test Conditions
The measurement was performed under the conditions of the feeding liquid for mobile phase conditions as follows. Mobile phase A: 0.05 mol/L aqueous sodium perchlorate solution at pH 2.5/acetonitrile (90:10) mixture Mobile phase B: 0.05 mol/L aqueous sodium perchlorate solution at pH 2.5/acetonitrile (40:60) mixture Feeding liquid for mobile phase: The concentration gradient was controlled by changing the mixing ratio of mobile phase A and mobile phase B as follows.

TABLE 3

| Time after injection (minutes) | Mobile phase A (vol %) | Mobile phase B (vol %) |
|---|---|---|
| 0-7 | 100 | 0 |
| 7-7.1 | 100 -> 0 | 0 -> 100 |
| 7.1-20 | 0 | 100 |

When liquid for dissolution (g), which is 0.1 mol/L hydrochloric acid/acetonitrile (7:3) mixture, was tried to be used to prepare a sample solution, it was found that the edaravone active pharmaceutical ingredient was soluble.

Figure 5:
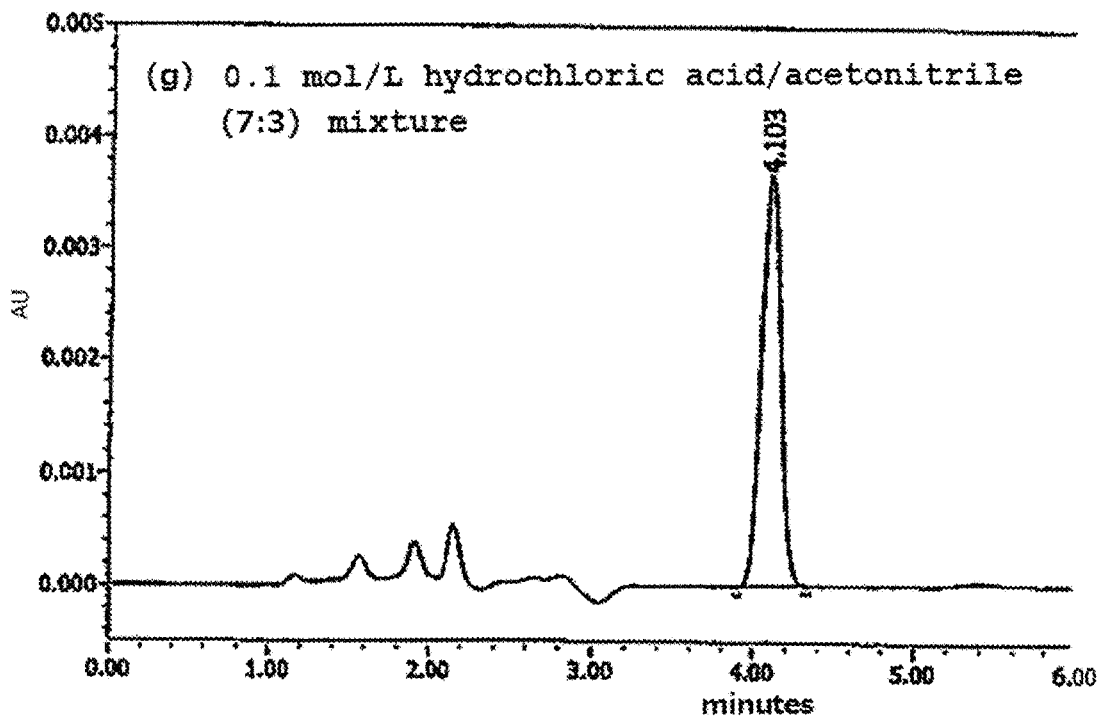
FIG. 5 is an HPLC chromatogram of a phenylhydrazine solution prepared with a 0.1 mol/L hydrochloric acid/acetonitrile (7:3) mixture.

The measurement results of the standard solutions prepared with liquid for dissolution (c) and liquid for dissolution (g) as described above are shown in Table 4 and FIGS. 1 and 5.

The test revealed that use of liquid for dissolution (g) enabled to provide any better peak shape of the phenylhydrazine solution.

Theoretical Plate Number and a Symmetry Coefficient

TABLE 4

Result of each standard solution

| liquids for dissolution | sample solutions | standard solutions | |
|---|---|---|---|
| | solubility of EDVP | theoretical plate number | symmetry coefficient |
| (c) 0.1 mol/L hydrochloric acid/acetonitrile (6:4) mixture | soluble | 3271 | 0.9 |
| (g) 0.1 mol/L hydrochloric acid/acetonitrile (7:3) mixture | soluble | 5563 | 1.0 |

Example 1

The edaravone active pharmaceutical ingredient (0.1020 g) was dissolved in a 0.1 mol/L hydrochloric acid/acetonitrile mixture (volume ratio 7:3; hereinafter referred to as Liquid for Dissolution), and the solution was adjusted exactly to 10 mL to prepare a first sample solution.

Separately, 13.693 mg of phenylhydrazine hydrochloride (about 10 mg as phenylhydrazine) was dissolved in Liquid for Dissolution, and the solution was adjusted exactly to 100 mL. To the solution measured precisely to 2 mL, Liquid for Dissolution was added, and the solution was adjusted exactly to 20 mL. To the solutions measured precisely to 2 mL, Liquid for Dissolution was added, and the solution was adjusted exactly to 20 mL to prepare a first standard solution (phenylhydrazine: 1 µg/mL).

Separately, 5 µL of phenylhydrazine was dissolved in Liquid for Dissolution, and the solution was adjusted exactly to 100 mL. To the solutions measured precisely to 1 mL, Liquid for Dissolution was added, and the solution was adjusted exactly to 10 mL. The resulting solution measured precisely to 1 mL was mixed with 0.1010 g of the edaravone active pharmaceutical ingredient, Liquid for Dissolution was added to the mixture, and the solution was adjusted exactly to 10 mL to prepare a first addition sample solution.

After a defined period of time, each 10 µL of the first standard solution, the first sample solution, and the first addition sample solution was precisely measured and collected, and was subjected to the test under the following conditions by high performance liquid chromatography, followed by measuring the peak area of phenylhydrazine (measured value of phenylhydrazine) in each solution according to the automatic integration process.

The phenylhydrazine content in the edaravone active pharmaceutical ingredient can be calculated by Equation 3 as shown below.

Test Conditions

Degassing of liquid for dissolution/nitrogen bubbling: None

Storage temperature of a first sample solution, a first standard solution and a first addition sample solution after preparation: 5° C.

Vessel (preparation and storage of a first sample solution, a first standard solution and a first addition sample solution): Brown glass bottle Detector: UV absorption photometer (measurement wavelength: 225 nm)

Column: Octadecyl silylated silica gel packed column (YMC-Pack Pro C18)

Column temperature: Constant temperature around 40° C.

Mobile phase: Concentration gradient controlled by starting from 100% mobile phase A up to 100% mobile phase B Mobile phase A: 0.05 mol/L aqueous sodium perchlorate solution at pH 2.5/acetonitrile (volume ratio 9:1) mixture Mobile phase B: 0.05 mol/L aqueous sodium perchlorate solution at pH 2.5/acetonitrile (volume ratio 2:3) mixture

*0.05 mol/L aqueous sodium perchlorate solution at pH 2.5: 7.0 g of sodium perchlorate was dissolved in 1000 mL of water, perchloric acid was added to the solution, and the pH of the resultant solution was adjusted to 2.5.

Figure 6:
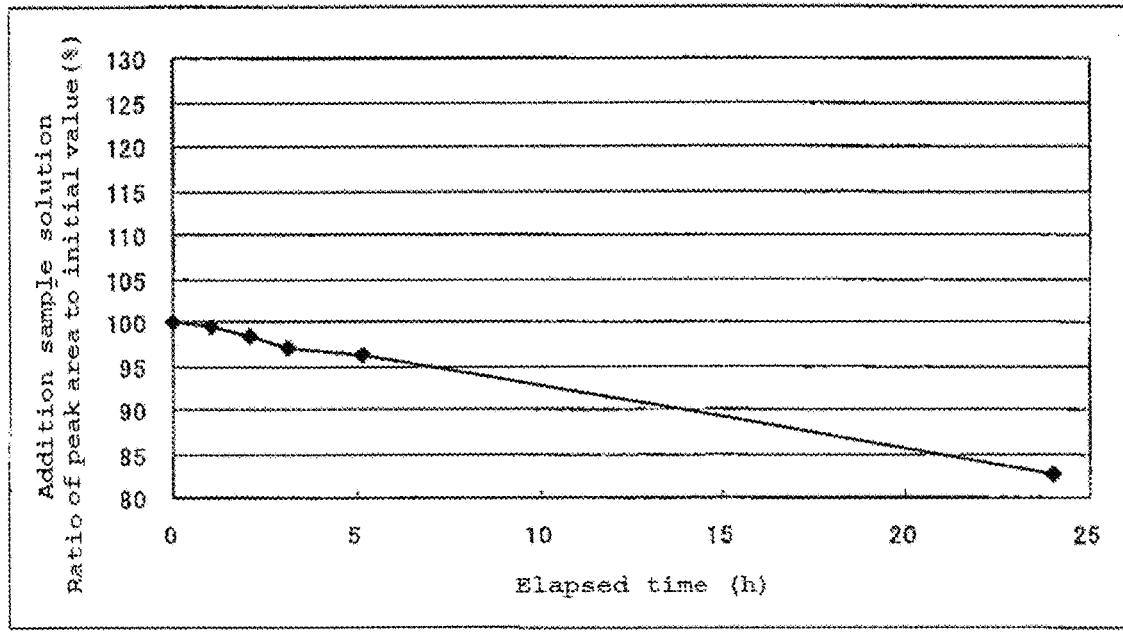
FIG. 6 is a graph showing the time-dependent changes in the ratio (%) of the peak area to the initial value of phenylhydrazine contained in an addition sample solution prepared with a 0.1 mol/L hydrochloric acid/acetonitrile (7:3) mixture.

The results of the stability study of phenylhydrazine and/or 3-methyl-1-phenyl-2-pyrazolin-5-one in the first standard solution, the first sample solution and the first addition sample solution are shown in Table 5 and FIG. 6.

TABLE 5

Stability of phenylhydrazine and/or 3-methyl-1-phenyl-2-pyrazolin-5-one in the solutions of a hydrochloric acid/acetonitrile mixture

| Solution | Elapsed time (h) | Peak area of phenylhydrazine (µV second) | Ratio to initial value (%) |
|---|---|---|---|
| First standard solution | 0.0 | 32018 | 100 |
|  | 9.3 | 32224 | 100.6 |
|  | 28.2 | 30139 | 94.1 |
| First sample solution | 0.0 | 0 |  |
|  | 1.0 | 0 |  |
|  | 2.1 | 0 |  |
|  | 3.1 | 0 |  |
|  | 5.1 | 0 |  |
|  | 24.1 | 534 | Content of phenylhydrazine: 1.7 ppm |
| First addition sample solution | 0.0 | 17313 | 100 |
|  | 1.0 | 17227 | 99.5 |
|  | 2.1 | 17042 | 98.4 |
|  | 3.1 | 16815 | 97.1 |
|  | 5.1 | 16639 | 96.1 |
|  | 24.0 | 14315 | 82.7 |

As to elapsed time (h), the time point at which the first standard solution, the first sample solution or the first addition sample solution was injected at the beginning into the HPLC within 30 minutes after preparing the solution was set as zero "0" hour of the elapsed time, and the subsequent elapsed times were calculated from the zero hour.

$$\text{Content of phenylhydrazine in an edaravone active pharmaceutical ingredient (ppm)} = M_S/M_T \times A_T/A_S \times 1 \times 0.748 \quad \text{Equation 3:}$$

where $M_S$: Weighed amount of phenylhydrazine hydrochloride in a first standard solution (mg)

$M_T$: Weighed amount of an edaravone active pharmaceutical ingredient in a first sample solution (g)

$A_T$: Peak area of phenylhydrazine in a first sample solution (µV second)

$A_S$: Peak area of phenylhydrazine in a first standard solution at 0 hour of the elapsed time (µV second)

0.748: Conversion factor from phenylhydrazine hydrochloride into phenylhydrazine The ratio of the peak area to the initial value of phenylhydrazine in the first standard solution was 90% or more even after 28 hours, showing that phenylhydrazine in the solution was stable.

Further, the ratio of the peak area to the initial value of phenylhydrazine in the first addition sample solution was 90% or more even after 5 hours, showing that phenylhydrazine, 3-methyl-1-phenyl-2-pyrazoline-5 in the solution was stable. Furthermore, in the first sample solution, the peak area of phenylhydrazine was not changed even after 5 hours, showing that 3-methyl-1-phenyl-2-pyrazolin-5-one in the solution was stable.

In addition, the use of the liquid for dissolution of 0.1 mol/L hydrochloric acid/acetonitrile mixture (volume ratio 7:3) enabled to dissolve completely the edaravone active pharmaceutical ingredient and phenylhydrazine, as well as to measure exactly the phenylhydrazine content in the solution.

Furthermore, the adoption of mobile phase A and mobile phase B as described above when performing HPLC enabled to reliably separate the edaravone active pharmaceutical ingredient contained in the solution. Further, the composition ratio of mobile phase A and mobile phase B as described above enabled to perform quantitative measurement without other peaks in the vicinity of the retention time of phenylhydrazine, and to elute the edaravone active pharmaceutical ingredient in the sample solution in a short time, leading to any efficient HPLC irrespective of involving in a two-step mobile phase.

From the above, it has been found that the method enables to accurately, quantitatively and easily measure the phenylhydrazine content in the edaravone active pharmaceutical ingredient without performing the complicated procedures such as degassing/nitrogen bubbling of liquid for dissolution nor measurement immediately after preparing the solution.

Example 2

Phenylhydrazine hydrochloride (13.517 mg, about 10 mg as phenylhydrazine) was dissolved in a 0.1 mol/L hydrochloric acid/acetonitrile mixture (volume ratio 7:3; hereinafter referred to as Liquid for Dissolution), and the solution was adjusted exactly to 100 mL. To the solution measured precisely to 2 mL, Liquid for Dissolution was added, and the solution was adjusted exactly to 20 mL. To the solution measured precisely to 2.5 mL, Liquid for Dissolution was added, and the solution was adjusted exactly to 100 mL to prepare a second standard solution (phenylhydrazine: 0.25 μg/mL).

Ten μL of the second standard solution was precisely measured and collected, and was subjected to the test by high performance liquid chromatography under the following conditions, followed by measuring the peak area of phenylhydrazine (measured value of phenylhydrazine) in the solution according to the automatic integration process.
Test Conditions
Degassing of liquid for dissolution/nitrogen bubbling: None
Storage temperature of a second sample solution and a second standard solution after preparation: 5° C.
Vessel (preparation and storage of a second sample solution and a second standard solution): Brown glass bottle
Detector: UV absorption photometer (measurement wavelength: 225 nm)
Column: Octadecyl silylated silica gel packed column (YMC-Pack Pro C18 or an equivalent column)
Column temperature: Constant temperature around 40° C.
Mobile phase: Concentration gradient controlled by starting from 100% mobile phase A up to 100% mobile phase B
Mobile phase A: 0.05 mol/L aqueous sodium perchlorate solution at pH 2.5/acetonitrile (volume ratio 9:1) mixture
Mobile phase B: 0.05 mol/L aqueous sodium perchlorate solution at pH 2.5/acetonitrile (volume ratio 2:3) mixture
*0.05 mol/L aqueous sodium perchlorate solution at pH 2.5: 7.0 g of sodium perchlorate was dissolved in 1000 mL of water, perchloric acid was added to the solution, and the pH of the resultant solution was adjusted to 2.5.
The result of the stability study of phenylhydrazine in the second standard solution is shown in Table 6.

TABLE 6

Stability of phenylhydrazine in the solutions of a hydrochloric acid/acetonitrile mixture

| Solution | Elapsed time (h) | Peak area of phenylhydrazine (μV second) | Ratio to initial value (%) |
|---|---|---|---|
| Second standard solution | 0.00 | 10016 | 100 |
| | 1.02 | 9872 | 98.6 |
| | 2.04 | 9820 | 98.0 |
| | 3.06 | 9693 | 96.8 |
| | 5.09 | 9113 | 91.0 |
| | 12.21 | 9328 | 93.1 |

As for the elapsed time (h), the time point at which the second standard solution was at the beginning injected into the HPLC within 30 minutes after preparing the solution was set as zero "0" hour of the elapsed time, and the subsequent elapsed times were calculated from the zero hour.

Further, when the second standard solution is used, the phenylhydrazine content contained in the edaravone active pharmaceutical ingredient in the first sample solution can be calculated by Equation 4.

$$\text{Content of phenylhydrazine in an edaravone active pharmaceutical ingredient (ppm)} = M_S/M_T \times A_T/A_S \times 0.25 \times 0.748 \quad \text{Equation 4}$$

where
$M_S$: Weighed amount of phenylhydrazine hydrochloride in a second standard solution (mg)
$M_T$: Weighed amount of an edaravone active pharmaceutical ingredient in a first sample solution (g)
$A_T$: Peak area of phenylhydrazine in a first sample solution (μV second)
$A_S$: Peak area of phenylhydrazine in a second standard solution at 0 hour of the elapsed time (μV second)
0.748: Conversion factor from phenylhydrazine hydrochloride into phenylhydrazine The ratio of the peak area to the initial value of phenylhydrazine in the second standard solution was 90% or more even after 12 hours, showing that phenylhydrazine in the solution was stable. In addition, it was revealed that the second standard solution as prepared in this example was enabled to use in the analysis method of the present invention, similarly to the first standard solution as prepared in Example 1.

From this, it has been found that the method enables to accurately, quantitatively and easily measure the phenylhydrazine content in the edaravone active pharmaceutical ingredient without performing complicated procedures such as degassing/nitrogen bubbling of liquid for dissolution nor measurement immediately after preparing the solution.

Example 3

The stability of phenylhydrazine and/or 3-methyl-1-phenyl-2-pyrazolin-5-one in a solution was investigated provided that an organic solvent in a liquid for dissolution was changed from acetonitrile to methanol.

Mixtures of 0.1 mol/L hydrochloric acid test liquid and methanol were prepared, and a liquid for dissolution was selected so that the ratio of organic solvent became lower in the range where EDVP was possibly dissolved (since the previous studies showed that a peak shape was improved when the ratio of organic solvent be close to that of the mobile phase). In accordance with the conditions of Example 1 other than the liquids for dissolution, the stability of phenylhydrazine and/or 3-methyl-1-phenyl-2-pyrazolin-5-one in the solutions was investigated.

Sample solutions were prepared with the following three liquids for dissolution.
1. 0.1 mol/L hydrochloric acid/methanol (7:3) mixture
2. 0.1 mol/L hydrochloric acid/methanol (6:4) mixture
3. 0.1 mol/L hydrochloric acid/methanol (5:5) mixture The results showed that EDVP was soluble in liquid for dissolution 3. Therefore, 0.1 mol/L hydrochloric acid/methanol (5:5) mixture was used to prepare the addition sample solution (edaravone active pharmaceutical ingredient: 0.10111 g, phenylhydrazine: 5 μL), the standard solution (phenylhydrazine hydrochloride: 13.154 mg), and the sample solution (edaravone active pharmaceutical ingredient: 0.10275 g), and the stability of the solutions was investigated.

The phenylhydrazine content in the edaravone active pharmaceutical ingredient can be determined by the method according to the calculation method based on Equation 3.

Figure 7:
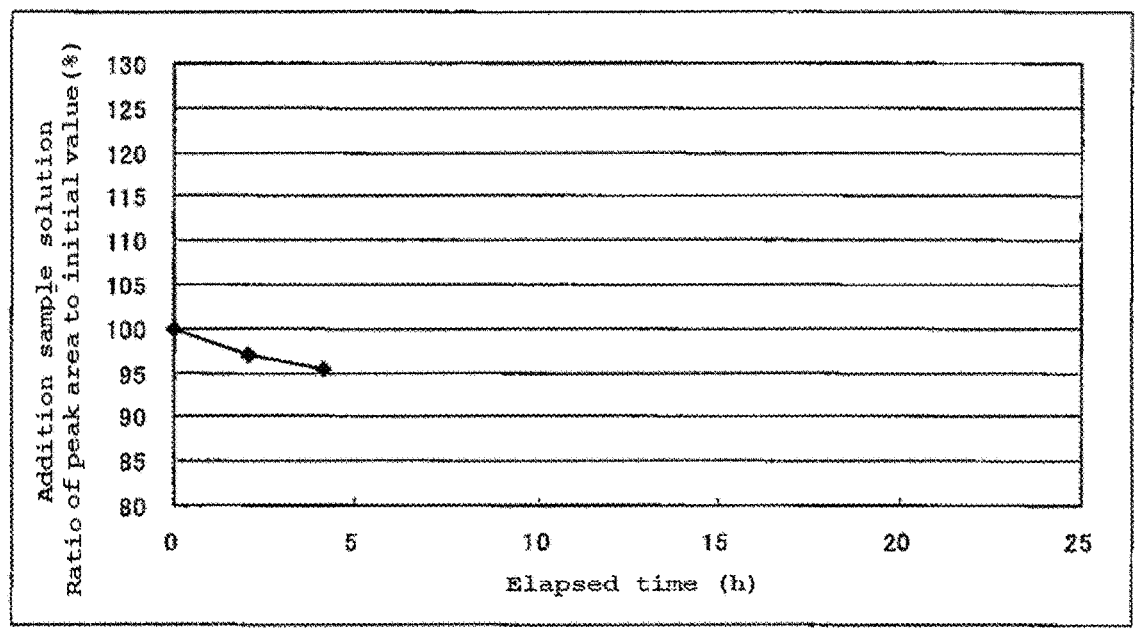
FIG. 7 is a graph showing the time-dependent changes in the ratio (%) of the peak area to the initial value of phenylhydrazine contained in an addition sample solution prepared with a 0.1 mol/L hydrochloric acid/methanol (5:5) mixture.

The results of the stability study of phenylhydrazine in the solution of 0.1 mol/L hydrochloric acid/methanol (5:5) mixture are shown in Table 7 and FIG. 7. The phenylhydrazine in the solution tended to be faster decomposed than the results of Example 1 as prepared using 0.1 mol/L hydrochloric acid/acetonitrile (7:3) mixture.

TABLE 7

Stability in the solutions using hydrochloric acid/methanol mixtures

| Solution | Elapsed time*[15] (h) | Peak area of phenylhydrazine (µV second) | Ratio to initial value (%) |
| --- | --- | --- | --- |
| Addition sample solution | 0.0 | 17853 | 100.0 |
| | 2.1 | 17343 | 97.1 |
| | 4.1 | 17057 | 95.5 |
| Standard solution | 0.0 | 34144 | 100.0 |
| | 2.1 | 33831 | 99.1 |
| | 4.1 | 33406 | 97.8 |
| | 10.3 | 31594 | 92.5 |
| Sample solution (Rot No. 240010) | 0.0 | 0 | |
| | 2.1 | 0 | |
| | 4.1 | 0 | |

*[15]As for the elapsed time (h), the time point at which the addition sample solution, the standard solution and the sample solution were at the beginning injected into the HPLC within 30 minutes after preparing the solutions was set as zero "0" hour of the elapsed time, and the subsequent elapsed times were calculated from the zero hour.

Phenylhydrazine is easily decomposed by light and oxygen. Therefore, in order to prevent the decomposition of phenylhydrazine in the solution, complicated procedures normally should be conducted such as degassing/nitrogen bubbling of a liquid for dissolution before the measurement, the measurement immediately after preparing the solution and the like. However, according to an embodiment of the present invention, it has been found that it is not necessary to perform degassing and nitrogen bubbling of a liquid for dissolution before the measurement, and that the decomposition of phenylhydrazine in the solution is enabled to be prevented for a long period of time.

The results of Examples 1 to 3 have demonstrated that the analysis method based on the embodiments of the present invention using a hydrochloric acid/acetonitrile mixture (liquid for dissolution) and a hydrochloric acid/methanol mixture (liquid for dissolution) enables to quantitatively and easily measure a phenylhydrazine content in an edaravone active pharmaceutical ingredient, without performing degassing and nitrogen bubbling of a liquid for dissolution, while preventing the decomposition of phenylhydrazine and the decomposition of 3-methyl-1-phenyl-2-pyrazolin-5-one in a solution for a long period of time.

A purpose of the present invention is to provide an analysis method for measuring phenylhydrazine contained in a 3-methyl-1-phenyl-2-pyrazolin-5-one active pharmaceutical ingredient accurately and simply.

Another purpose of the present invention is to provide a method of treating amyotrophic lateral sclerosis and of suppressing progress of amyotrophic lateral sclerosis using a medicament containing a 3-methyl-1-phenyl-2-pyrazolin-5-one active pharmaceutical ingredient in which the phenylhydrazine content is strictly controlled.

Further, another purpose of the present invention is to provide a method of producing a medicament containing a 3-methyl-1-phenyl-2-pyrazolin-5-one active pharmaceutical ingredient in which the phenylhydrazine content is strictly controlled.

A method of analyzing the phenylhydrazine content in a 3-methyl-1-phenyl-2-pyrazolin-5-one active pharmaceutical ingredient according to an embodiment of the present invention, includes obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 µg/mL to 10 µg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, and detecting the phenylhydrazine content in the 3-methyl-1-phenyl-2-pyrazolin-5-one active pharmaceutical ingredient on the basis of the first measured value and the second measured value. The first acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the first water-soluble organic solvent is at least one type selected from the group consisting of acetonitrile and methanol, provided that, when the first water-soluble organic solvent is methanol, the first acidic water is at least one type selected from the group consisting of hydrochloric acid, an aqueous acetic acid solution, an aqueous trifluoroacetic acid solution, an aqueous formic acid solution and an aqueous perchloric acid solution, and the second acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one type selected from the group consisting of acetonitrile and methanol, provided that, when the second water-soluble organic solvent is methanol, the second acidic water is at least one type selected from the group consisting of hydrochloric acid, an aqueous acetic acid solution, an aqueous trifluoroacetic acid solution, an aqueous formic acid solution and an aqueous perchloric acid solution.

A method of treating amyotrophic lateral sclerosis according to another embodiment of the present invention includes obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 µg/mL to 10 µg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, detecting the phenylhydrazine content in the 3-methyl-1-phenyl-2-pyrazolin-5-one active pharmaceutical ingredient on the basis of the first measured value and the second measured value, to determine that the phenylhydrazine content is 20 ppm or less, and administering a medicament containing the 3-methyl-1-phenyl-2-pyrazolin-5-one active pharmaceutical ingredient to a patient in need. The first acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the first water-soluble organic solvent is at least one type selected from the group consisting of acetonitrile and methanol, provided that, when the first water-soluble organic solvent is methanol, the first acidic water is at least one type selected from the group consisting of hydrochloric acid, an aqueous acetic acid solution, an aqueous trifluoroacetic acid solution, an aqueous formic acid solution and an aqueous perchloric acid solution, and the second acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one type selected from the group consisting of acetonitrile and methanol, provided that, when the second water-soluble organic solvent is methanol, the second acidic water is at least one type selected from the group consisting of hydrochloric acid, an aqueous acetic acid solution, an aqueous trifluoroacetic acid solution, an aqueous formic acid solution and an aqueous perchloric acid solution.

A method of suppressing progress of amyotrophic lateral sclerosis according to yet another embodiment of the present invention includes obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 μg/mL to 10 μg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, detecting the phenylhydrazine content in the 3-methyl-1-phenyl-2-pyrazolin-5-one active pharmaceutical ingredient on the basis of the first measured value and the second measured value, to determine that the phenylhydrazine content is 20 ppm or less, and administering a medicament containing the 3-methyl-1-phenyl-2-pyrazolin-5-one active pharmaceutical ingredient to a patient in need. The first acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the first water-soluble organic solvent is at least one type selected from the group consisting of acetonitrile and methanol, provided that, when the first water-soluble organic solvent is methanol, the first acidic water is at least one type selected from the group consisting of hydrochloric acid, an aqueous acetic acid solution, an aqueous trifluoroacetic acid solution, an aqueous formic acid solution and an aqueous perchloric acid solution, and the second acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one type selected from the group consisting of acetonitrile and methanol, provided that, when the second water-soluble organic solvent is methanol, the second acidic water is at least one type selected from the group consisting of hydrochloric acid, an aqueous acetic acid solution, an aqueous trifluoroacetic acid solution, an aqueous formic acid solution and an aqueous perchloric acid solution.

A method of producing a medicament containing a 3-methyl-1-phenyl-2-pyrazolin-5-one active pharmaceutical ingredient having a phenylhydrazine content of 20 ppm or less according to still another aspect of the present invention includes obtaining a first measured value by measuring the phenylhydrazine content in a phenylhydrazine standard solution that contains phenylhydrazine or a salt thereof, a first acidic water and a first water-soluble organic solvent, and that exhibits a phenylhydrazine concentration of 0.01 μg/mL to 10 μg/mL, obtaining a second measured value by measuring the phenylhydrazine content in a 3-methyl-1-phenyl-2-pyrazolin-5-one sample solution that contains a 3-methyl-1-phenyl-2-pyrazolin-5-one active pharmaceutical ingredient, a second acidic water and a second water-soluble organic solvent, detecting the phenylhydrazine content in the 3-methyl-1-phenyl-2-pyrazolin-5-one active pharmaceutical ingredient on the basis of the first measured value and the second measured value, to determine that the phenylhydrazine content is 20 ppm or less, and mixing the 3-methyl-1-phenyl-2-pyrazolin-5-one active pharmaceutical ingredient with at least one pharmacologically and pharmaceutically acceptable additive. The first acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the first water-soluble organic solvent is at least one type selected from the group consisting of acetonitrile and methanol, provided that, when the first water-soluble organic solvent is methanol, the first acidic water is at least one type selected from the group consisting of hydrochloric acid, an aqueous acetic acid solution, an aqueous trifluoroacetic acid solution, an aqueous formic acid solution and an aqueous perchloric acid solution, and the second acidic water is at least one type selected from the group consisting of hydrochloric acid, an aqueous acetic acid solution, an aqueous trifluoroacetic acid solution, an aqueous formic acid solution, an aqueous phosphoric acid solution and an aqueous perchloric acid solution, and the second water-soluble organic solvent is at least one type selected from the group consisting of acetonitrile and methanol, provided that, when the second water-soluble organic solvent is methanol, the second acidic water is at least one type selected from the group consisting of hydrochloric acid, an aqueous acetic acid solution, an aqueous trifluoroacetic acid solution, an aqueous formic acid solution and an aqueous perchloric acid solution.

According to the present invention, it is possible to provide an analysis method for measuring phenylhydrazine contained in a 3-methyl-1-phenyl-2-pyrazolin-5-one active pharmaceutical ingredient accurately and simply.

Further, according to the present invention, it is possible to provide a method of treating amyotrophic lateral sclerosis and of suppressing progress of amyotrophic lateral sclerosis which comprises using a medicament containing a 3-methyl-1-phenyl-2-pyrazolin-5-one active pharmaceutical ingredient in which the phenylhydrazine content is strictly controlled.

Furthermore, according to the present invention, it is possible to provide a method of producing a medicament containing a 3-methyl-1-phenyl-2-pyrazolin-5-one active pharmaceutical ingredient in which the phenylhydrazine content is strictly controlled.

Obviously, numerous modifications and variations of the present invention are possible in light of the above teachings. It is therefore to be understood that with the scope of the appended claims, the invention may be practiced otherwise than as specifically described herein.

The invention claimed is:

1. A method of analyzing a phenylhydrazine content in a 3-methyl-1-phenyl-2-pyrazolin-5-one active pharmaceutical ingredient, comprising:
   obtaining a first measured value by measuring a phenylhydrazine content in a phenylhydrazine standard solution including phenylhydrazine or a salt thereof, a first acidic water and a first water-soluble organic solvent and having a phenylhydrazine concentration in a range of 0.01 μg/mL to 10 μg/mL;
   obtaining a second measured value by measuring a phenylhydrazine content in a 3-methyl-1-phenyl-2-pyrazolin-5-one sample solution including a 3-methyl-1-phenyl-2-pyrazolin-5-one active pharmaceutical ingredient, a second acidic water and a second water-soluble organic solvent; and
   detecting a phenylhydrazine content in a 3-methyl-1-phenyl-2-pyrazolin-5-one active pharmaceutical ingredient based on the first measured value and the second measured value,
   wherein the first acidic water includes hydrochloric acid and has an acid concentration in a range of 0.01 mol/L to 1 mol/L, the first water-soluble organic solvent is at least one selected from the group consisting of acetonitrile and methanol and has a volume ratio of the first acidic water and the first water-soluble organic solvent in the phenylhydrazine standard solution in a range of 9:1 to 6:1 such that the phenylhydrazine or a salt thereof is soluble in the phenylhydrazine standard solution, the second acidic water includes hydrochloric acid and has an acid concentration in a range of 0.01 mol/L to 1 mol/L, and the second water-soluble organic solvent is at least one selected from the group consisting of acetonitrile and methanol and has a volume ratio of the second acidic water and the second water-soluble organic solvent in the 3-methyl-1-phenyl-2-pyrazoline-5-one sample solution in a range of 9:1 to 6:1 such that the 3-methyl-1-phenyl-2-pyrazolin-5-one active pharmaceutical ingredient is soluble in the 3-methyl-1-phenyl-2-pyrazolin-5-one sample solution.

2. The method according to claim 1, further comprising:
   preparing the phenylhydrazine standard solution; and
   preparing the 3-methyl-1-phenyl-2-pyrazolin-5-one sample solution.

3. The method according to claim 1, wherein the first measured value is obtained by measuring the phenylhydrazine content in the phenylhydrazine standard solution using high performance liquid chromatography, and the second measured value is obtained by measuring the phenylhydrazine content in the 3-methyl-1-phenyl-2-pyrazolin-5-one sample solution using high performance liquid chromatography.

4. The method according to claim 1, wherein the first water-soluble organic solvent includes methanol, and the second water-soluble organic solvent includes acetonitrile.

5. The method according to claim 1, wherein the acid concentration of the first acidic water is 0.01 mol/L, and the acid concentration of the second acidic water is 0.01 mol/L.

6. The method according to claim 5, wherein the first water-soluble organic solvent has the volume ratio of the first acidic water and the first water-soluble organic solvent in the phenylhydrazine standard solution such that a symmetry coefficient for a peak of phenylhydrazine in high performance liquid chromatography is 0.9 or higher.

7. The method according to claim 2, wherein the first measured value is obtained by measuring the phenylhydrazine content in the phenylhydrazine standard solution using high performance liquid chromatography, and the second measured value is obtained by measuring the phenylhydrazine content in the 3-methyl-1-phenyl-2-pyrazolin-5-one sample solution using high performance liquid chromatography.

8. The method according to claim 2, wherein the first water-soluble organic solvent includes methanol, and the second water-soluble organic solvent includes acetonitrile.

9. The method according to claim 2, wherein the acid concentration of the first acidic water is 0.01 mol/L, and the acid concentration of the second acidic water is 0.01 mol/L.

10. The method according to claim 9, wherein the first water-soluble organic solvent has the volume ratio of the first acidic water and the first water-soluble organic solvent in the phenylhydrazine standard solution such that a symmetry coefficient for a peak of phenylhydrazine in high performance liquid chromatography is 0.9 or higher.

11. The method according to claim 3, wherein the first water-soluble organic solvent includes methanol, and the second water-soluble organic solvent includes acetonitrile.

12. The method according to claim 3, wherein the acid concentration of the first acidic water is 0.01 mol/L, and the acid concentration of the second acidic water is 0.01 mol/L.

13. The method according to claim 12, wherein the first water-soluble organic solvent has the volume ratio of the first acidic water and the first water-soluble organic solvent in the phenylhydrazine standard solution such that a symmetry coefficient for a peak of phenylhydrazine in high performance liquid chromatography is 0.9 or higher.

14. The method according to claim 4, wherein the acid concentration of the first acidic water is 0.01 mol/L, and the acid concentration of the second acidic water is 0.01 mol/L.

15. The method according to claim 14, wherein the first water-soluble organic solvent has the volume ratio of the first acidic water and the first water-soluble organic solvent in the phenylhydrazine standard solution such that a symmetry coefficient for a peak of phenylhydrazine in high performance liquid chromatography is 0.9 or higher.

16. The method according to claim 7, wherein the first water-soluble organic solvent includes methanol, and the second water-soluble organic solvent includes acetonitrile.

17. The method according to claim 7, wherein the acid concentration of the first acidic water is 0.01 mol/L, and the acid concentration of the second acidic water is 0.01 mol/L.

18. The method according to claim 17, wherein the first water-soluble organic solvent has the volume ratio of the first acidic water and the first water-soluble organic solvent in the phenylhydrazine standard solution such that a symmetry coefficient for a peak of phenylhydrazine in high performance liquid chromatography is 0.9 or higher.

19. The method according to claim 16, wherein the acid concentration of the first acidic water is 0.01 mol/L, and the acid concentration of the second acidic water is 0.01 mol/L.

20. The method according to claim 19, wherein the first water-soluble organic solvent has the volume ratio of the first acidic water and the first water-soluble organic solvent in the phenylhydrazine standard solution such that a symmetry coefficient for a peak of phenylhydrazine in high performance liquid chromatography is 0.9 or higher.

* * * * *